United States Patent [19]
Keisling et al.

[11] 3,982,896
[45] Sept. 28, 1976

[54] TEST METHOD FOR DETERMINING ZEOLITE

[75] Inventors: Charles A. Keisling, Boylston; Leonard B. Sand, Holden, both of Mass.

[73] Assignee: Zeochem Corporation, Worcester, Mass.

[22] Filed: Nov. 4, 1974

[21] Appl. No.: 520,296

[52] U.S. Cl. ............................. 23/230 R; 23/259; 73/15 R; 177/164
[51] Int. Cl.² ................. G01N 25/00; G01N 25/20; G01G 3/08
[58] Field of Search ................... 23/230 R; 73/15 R

[56] References Cited
OTHER PUBLICATIONS
Chemical Abstracts, 75:80403v, (1971).
Chemical Abstracts, 78:62660j, (1973).
Chemical Abstracts, 79:10532v, (1973).

Primary Examiner—Morris O. Wolk
Assistant Examiner—Sidney Marantz
Attorney, Agent, or Firm—Norman S. Blodgett; Gerry A. Blodgett

[57] ABSTRACT

A test method for determining the amount of zeolite material in a sample comprising heating a weighed portion of the sample to remove adsorbed water, cooling the heated portion, adding a known quantity of water to the portion, noting the resulting temperature rise and correlating the temperature rise to the amount of zeolite material in the sample. The test can be carried out in the field with a kit which includes a weighing device.

2 Claims, 6 Drawing Figures

3,982,896

TEST METHOD FOR DETERMINING ZEOLITE

BACKGROUND OF THE INVENTION

Since the discovery in the 1950's of large deposits of zeolites occuring as small (25μm) crystals in altered siliceous pyroclastics and flows, it has been recognized that a simple field test for determining the presence and percent of zeolite content would be useful for exploration and mining. A test to detect the presence of zeolite was reported by Helfferich (1964) using a combination of ion exchange and pH measurement. In arid regions the presence of zeolite in an ash bed or flow often can be determined by the heat generated when touching a sample to the tip of the tongue or on a wet spot in the palm of the hand. If the climate is humid or the deposit wet, a small sample can be heated over a lighter, cooled in a closed container, and then tested for the heat generated on the tongue or hand. To ascertain the quality of the deposit it has been necessary to rely completely on laboratory tests such as X-ray diffraction, sorption capacity and quantitative ion exchange determinations which are not available to some and in any case cause lag time in the field even if liaison with the laboratory is arranged or because additional field trips must be made after collection and laboratory evaluation. Thus, these methods are either not quantitative or are expensive, complicated and require extensive stationary equipment and highly trained personnel. These and other difficulties experienced with the prior art devices have been obviated in a novel manner by the present invention.

It is, therefore, an outstanding object of the invention to provide a field kit which allows on-site, quantitative analysis of molecular sieve zeolite deposits.

Another object of this invention is the provision of a field kit which is simple and rugged.

A further object of the present invention is the provision of a field kit which is sufficiently accurate to replace or beneficially cooperate with other techniques.

It is another object of the instant invention to provide a field kit which is simple and easy to carry, use, and maintain.

A still further object of the invention is the provision of a field kit which can be made inexpensively and which is capable of a long and useful life.

With these and other objects in view, as will be apparent to those skilled in the art, the invention resides in the combination of parts set forth in the specification and covered by the claims appended hereto.

SUMMARY OF THE INVENTION

This invention involves a field kit and method determining quantitatively the molecular sieve zeolite content of a natural or synthetic sample. The kit includes a rugged, high-precision weight scale for separating a specific mass of sample, a heater for heating the sample to a temperature at which absorbed water is desorped and a sealable container for isolating the mass of sample from the atmosphere. In addition, the kit includes a measuring means for separating a specific quantity of water to be added to the mass, and a thermometer to measure the increase in temperature of the mass and water mix. The weight scale is formed of an elongated phosphor bronze flat spring.

BRIEF DESCRIPTION OF THE DRAWINGS

The character of the invention, however, may be best understood by reference to one of its structural forms, as illustrated by the accompanying drawings, in which.

DESCRIPTION OF THE PREFERRED EMBODIMENT

Molecular sieve zeolites have several unique properties which make it possible to distinguish them from other fine-grained minerals and even other zeolites such as analcime. The molecular sieve zeolites contain intracrystalline pores which are interconnected to the crystal surfaces by ports of 8-, 10-, or 12-membered rings of oxygens. Their porous crystal structure gives them high sorptive capacities to 50% pore volume or to 30 wt.% water sorbed (with accompanying high heats of sorption or immersion up to 100 cal/gm) and selective sorption of smaller molecules, such as water and $CO_2$, with exclusion of larger molecules. Being network aluminosilicates, the $Al^{3+}$ for $Si^{4+}$ substitutions provide active sites for exchangeable cations located in the crystal pores. As with other minerals the zeolites are best identified by X-ray diffraction analysis, but the instrument is too expensive and bulky for general field use. The optical properties of the very small zeolite crystals are not readily distinguishable with the polarizing microscope.

The diagnostic property of high heat of immersion, as used qualitatively to detect the presence of zeolite, was selected as most suitable for a quantitative field test. Barrer and Cram (1971) recently have reported on results of laboratory experiments on heats of immersion of outgassed synthetic (with some natural) molecular sieve zeolites in various ion exchanged forms.

Figure 1:
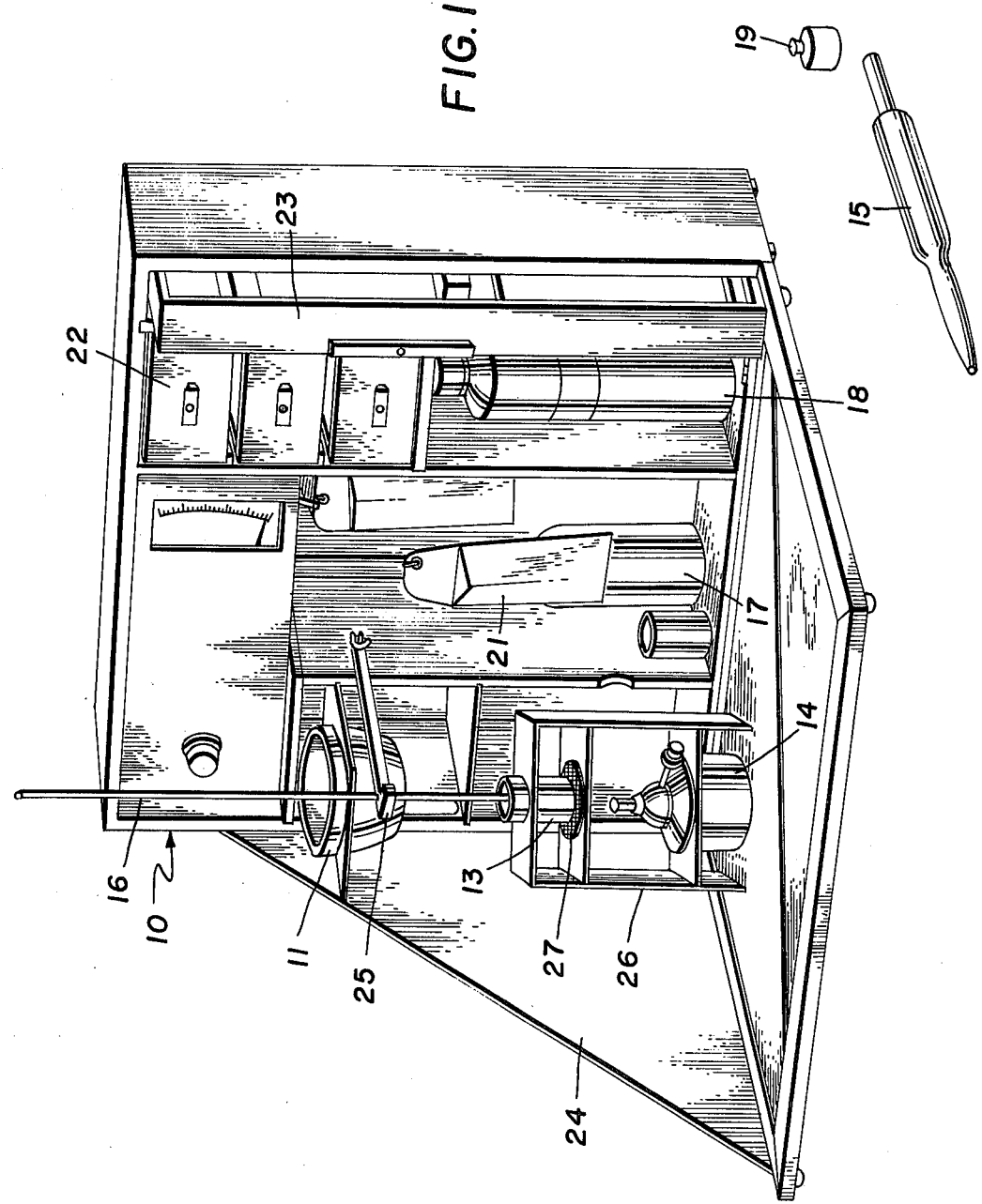
FIG. 1 is a perspective view of a field kit embodying the principles of the present invention.

In a preferred embodiment of the invention, the field kit 10 designed weighs 20 lbs. and is shown in FIG. 1. To use the working data given in this disclosure the unit would have to be duplicated. However, a different design can be used and other working data determined with zeolite reference standards. The kit is composed of a mortar and pestle 11 to disaggregate the sample; a rugged, easily constructed phosphor bronze flat spring balance 12 to weight 5 gms. of sample to ±0.02 gms.; a 35 mm. film cannister 13 or other suitable container to contain the sample; an alcohol burner 14 to activate the sample by driving off the intracrystal pore water; a 10 ml. volumetric pipette 15 to measure the given volume of water; a thermometer 16 with 0.2°C divisions to measure the temperature rise due to heat of immersion; and polyethylene bottles 17 and 18 of alcohol and water. A can of alcohol must be carried separately as one test uses 30 ml. of alcohol. Vials of reference zeolite samples a 5 gm. weight 19, weighing envelopes 21 and extra cannisters are carried in the drawers 22. The thermometer and pipette with spares are cushion-mounted in the vertical drawer 23. The side windbreakers 24 attach to make the opened door right angles to the rest of the unit. A spring-tensioned sleeve 25 is used to hold the thermometer in position when measuring the temperature rise, ΔT, from the heat of immersion. The dimensions of the heater assembly 26 are such that the bottom of the sample cannister resting on an asbestos-covered wire screen 27 is 2-⅜ inches (6 cm) above the metal tip of the alcohol burner 14 when fully opened.

An important part of this system is the weight balance which must be both rugged and extremely precise. In order to accomplish these two somewhat inconsistent objectives, the scale was designed to accurately indicated a single predetermined weight. The scale is zeroed with a standard weight and then the standard is removed and a quantity of sample is placed on the scale to return the scale to zero. Using this scheme, most error causing factors are eliminated at the single weight.

Figure 2:
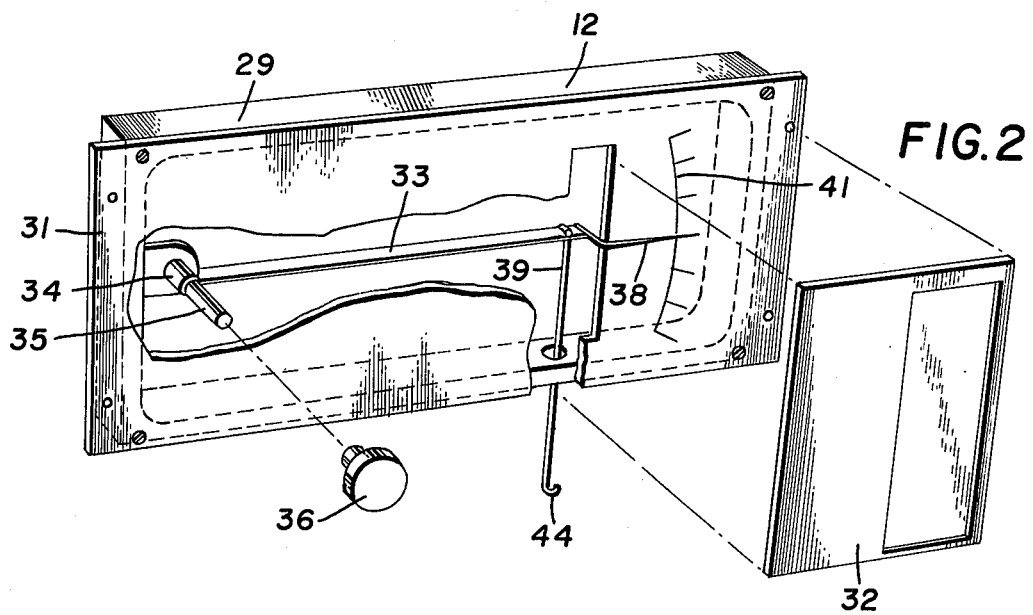
FIG. 2 is an expanded and cut-away perspective view of a weight scale embodying the principles of the present invention.

Referring to FIG. 2, the weight scale 12 is shown to include a case 28 with a box 29, a face plate 31, and a window plate 32. Within the case is an elongated, flat phosphor bronze spring 33 of dimensions 6- ½ inches × ¼ inches × 0.015 inches. One end of the spring is rigidly attached to a clamp 34 which is mounted between the box 29 and the face plate 31 for rotation about an axis perpendicular to the length of the spring and in the plane of the springs width. The clamp is generally cylindrical and split parallel to its axis. The spring is clamped between the two halves. The clamp 34 is rigidly mounted for the above-mentioned rotation on zero adjust shaft 35 on which is connected zero adjust knob 36. The turning of the knob 36 turns the shaft 35, the clamp 34, and the spring 33.

Figure 4:
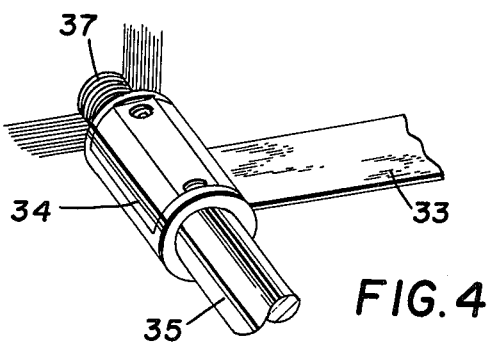
FIG. 4 is a detailed perspective view of a portion of the weight scale shown in FIG. 2.

As shown in FIG. 4, the zero adjust shaft 35 extends from the clamp 34 both forward through the face plate 31 and rearward slightly into an aperture in the box 29. Also threaded into the aperture is a set screw 37 having a friction surface which frictionally engages a friction surface on the end of the shaft 35. The frictional engagement can be adjusted to set the amount of torque necessary to rotate the shaft above that which would be caused by the spring but below that which could be applied through the knob 36.

Returning to FIG. 2, at the other end of the spring are a pointer 38 and a weight support rod 39. The pointer 38 is an L-shaped wire with one leg soldered to the spring. The other leg is extended through a slot in the face plate and is movable over gradation marks 41 in the face plate. One of the gradation marks in the set point or zero. The pointer, the slot in the face plate, and the marks are covered by the window plate through which the pointer and marks are visible.

Figure 3:
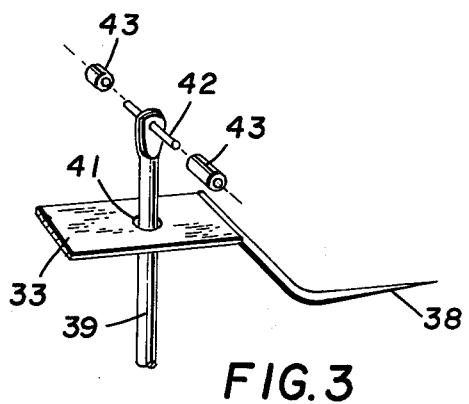
FIG. 3 is a detailed perspective view of a portion of the weight scale shown in FIG. 2.

As shown in FIG. 3, the weight support rod 39 is attached to the spring 33 by passing the rod 39 through an aperture 41 in the spring. A shaft 42 is passed through the rod 39 and tubes 43 fixed to the shaft 42. The other end of the rod 39 has a hook 44 from which an envelope can be hung.

The use and operation of the invention will now be readily understood in view of the above description. The sample is ground in the mortar to below 10 mesh (1/16inch) size. An envelope 21 is then hung from the hook 44 of the weight support rod 39 as shown in FIG. 1. A 5 gram standard weight 19 is placed in the envelope and the zero adjust knob turned so that the pointer 38 is over the set point. The standard weight is removed from the envelope, and a sufficient quantity of ground sample is placed in the envelope to return the pointed to the set point.

The contents of the envelope is placed in the thin-walled aluminum container and heated to 350°C over the burner with the mounted thermometer inserted midway into the sample. When this temperature is reached, the sample container is removed from the burner, capped with its cover and set aside to cool to atmospheric temperature. For rapid cooling the sample container can be set in water. The cover is removed, and the temperature ($T_s$) of the sample is measured to within 0.2°C. Ten ml. of water at a temperature ($T_w$) (preferably at atmospheric temperature) are poured on the sample and stirred quickly with the thermometer. The temperature of the mixture rises rapidly reaching a maximum value ($T_{max}$) within 30 seconds, then slowly dropping to atmospheric temperature. A high temperature rise upon the addition of water is characteristic of the presence of zeolitic material in the solid sample, and the degree of temperature rise is directly proportional to the quantity of zeolite present in the sample.

When the sample and water added to the sample are both at atmospheric temperature, the temperature rise is given by $$T = T_{max} - T_s$$

Under the test conditions in the field, it might be difficult to bring the activated sample and the water to be added to the exact same temperature. In this case the equivalent temperature rise, $\Delta T_{eq}$, can be otained from the following equation, assuming an average specific heat of 0.22 cal/g-°C for the solid sample:

$$\Delta T_{eq} = \frac{1.1(T_{max}-T_s) + 10(T_{max}-T_w)}{11.1}$$

Figure 5:
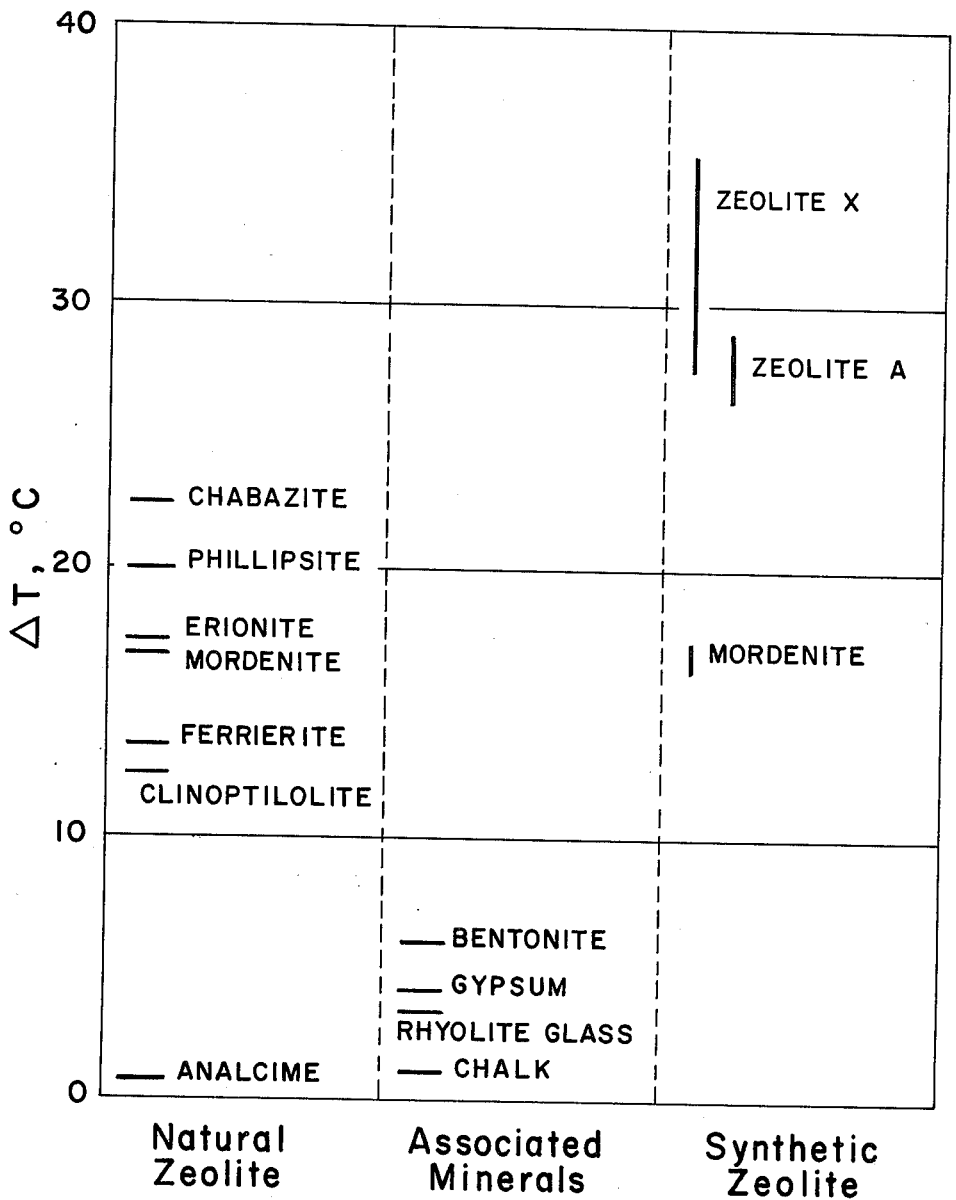
FIG. 5 is a graph of the temperature rise of various minerals.

The important, naturally occuring zeolite and commonly associated minerals as well as several commercial synthetic zeolites were tested. The temperature rises determined with this test method are graphed in FIG. 5. The purity of the sample was determined independently by X-ray powder diffraction analysis and adsorption capacity determinations.

Figure 6:
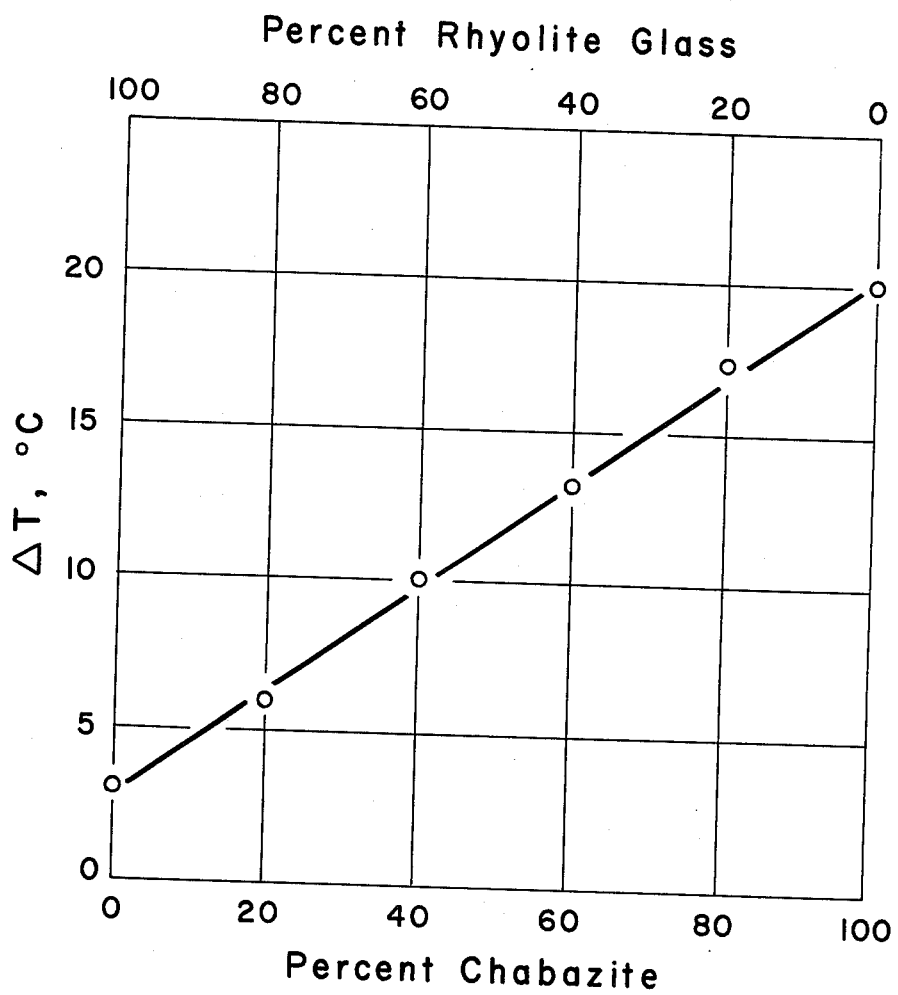
FIG. 6 is a graph of the temperature rise of various samples.

The degree of temperature rise was determined to be directly proportional to the purity of the zeolite by testing prepared mixtures of the zeolite chabazite and rhyolite volcanic glass, the usual parent material for zeolite crystallization in continental deposits and therefore the most common impurity in the zeolite deposits. The linear relationship obtained is shown in FIG. 6.

When testing an unknown sample from a new deposit, a temperature rise in the range of 4° to 8°C would determine the presence of zeolite but probably not in sufficient quantity to be of interest. A temperature rise above 20°C would indicate immediately a high grade chabazite-containing deposit, while a rise between 8°-20°C would indicate an intermediate to high grade deposit depending on the zeolite variety or varieties present. If possible to obtain, identification of the zeolites by X-ray diffraction analysis would be helpful at this point and the field testing can be completed on a quantitative basis.

The field kit has been found to be the most practical and quantitative test available for zeolite exploration. It is believed to have potential use also in mining operations and in the production of synthetic zeolites as a simple quality control test.

Even though Barrer and Cram have determined that the variations of heats of immersion for a given zeolite are primarily a function of the exchangeable cation (and the amount of residual presorbed water), synthetic zeolites do not vary in the kind (usually pure Na form) and amount of exchange cations. Barrer and Cram found variations in heats of immersion for a given zeolite, but the activation procedure in this field test was found to reproducibly activate the zeolite. This test gives results 5 to 30% less than the heats of immersion determined by Barrer and Cram, which reflects both the amount of heat losses unaccounted for in this simplified test as well as variations in the degree of outgassing and in differences in the exchangeable cation content. Even so, it should be noted that a precison of ±0.5° is obtained on subsamples. On a sample containing a zeolite giving a 30° temperature rise in the pure form the zeolite content can be measured to an accuracy of ±3%. This often is adequate for production quality control, and certainly more than adequate for a field exploration and mining test. Even for those laboratory researchers not equipped with elaborate sorption apparatus, it could serve as a diagnositc screening test for the zeolite activity following process testing procedures.

With the exception of analcime, which presently is not regarded as a molecular sieve zeolite, the naturally occurring zeolites exhibit a temperature rise of 12 to 23°C under the conditions of the test. A deposit containing 60% zeolite formed by the alteration of volcanic glass would give a ΔT of 10° to 18°C depending on the variety of zeolite present. In a deposit partially altered to zeolite, the partially altered glass (palagonite) even though X-ray amorphous, has been hydrolyzed sufficiently to contribute to the temperature rise. The other common impurities, bentonite and gypsum, wich significant heats of immersion usually can be identified in the hand specimen when present in more than minor amounts.

A single test requires one-half hour to complete, but in an 8-hour span thirty to forty tests can be carried out, for as one sample is being activated and cooled another is being tested for temperature rise.

It is obvious that minor changes may be made in the form and construction of the invention without departing from the material spirit thereof. It is not, however, desired to confine the invention to the exact form herein shown and described, but it is desired to include all such as properly come within the scope claimed.

REFERENCES

Barrer, R. M., and P. J. Cram (1971) Heats of immersion of outgassed ion-exchanged zeolites, In R. F. Gould (ed.) Molecular Sieve Zeolites-II, Advances in Chemistry Series 102, Washington, D.C. 131.

Helfferich, F. D. (1964) A simple identification reaction for zeolites (molecular sieves), Am. Mineral., 49, 1752–1754.

The invention having been thus described, what is claimed as new and desired to secure by Letters Patent is:

1. A test method for determining the amount of zeolite material in a sample, comprising the sequential steps of
    a. separating a specific mass of the sample,
    b. heating the mass to a temperature sufficient to desorb adsorbed water,
    c. isolating the heated mass from the atmosphere,
    d. cooling the isolated and heated mass,
    e. adding a specific quantity of adsorbable liquid to the mass,
    f. noting the rise in temperature of the mass and liquid mixture, and
    g. correlating the rise in temperature to the amount of zeolite material in the sample.

2. A method as recited in claim 1, wherein the separating of the specific mass of the sample is accomplished by setting a weighing device at a set-point with a standard weight, removing the standard weight from the weighing device, and then placing a quantity of the sample on the weighing device to return it to the set-point.

* * * * *